United States Patent [19]

Hoeksema et al.

[11] 4,331,659
[45] May 25, 1982

[54] ANTIBIOTIC U-62,162 AND PROCESS OF MAKING

[75] Inventors: Herman Hoeksema; Libor Slechta, both of Kalamazoo, Mich.

[73] Assignee: The Upjohn Company, Kalamazoo, Mich.

[21] Appl. No.: 185,130

[22] Filed: Sep. 10, 1980

[51] Int. Cl.³ .................. A61K 35/00; C12P 1/06; C12R 1/465; A61K 35/74
[52] U.S. Cl. ............................ 424/122; 424/121; 435/169; 435/886
[58] Field of Search .................. 435/169, 170, 253; 424/121, 122, 123, 124

[56] References Cited

U.S. PATENT DOCUMENTS 3,499,078 3/1970 Luedemann et al. ............... 424/118

Primary Examiner—Alvin E. Tanenholtz
Assistant Examiner—J. Martinell
Attorney, Agent, or Firm—Roman Saliwanchik

[57] ABSTRACT

Novel antibiotic U-62,162 producible in a fermentation under controlled conditions using a man-made biologically pure culture of the microorganism *Streptomyces verdensis*, Dietz and Li sp.n., NRRL 12256. This antibiotic is strongly active against various Gram-positive bacteria, for example, *Staphylococcus aureus*. Thus, antibiotic U-62,162 can be used in various environments to eradicate or control such bacteria.

8 Claims, 4 Drawing Figures

ANTIBIOTIC U-62,162 AND PROCESS OF MAKING

BRIEF SUMMARY OF THE INVENTION

Antibiotic U-62,162 is producible in a fermentation under controlled conditions using a biologically pure culture of the new microorganism *Streptomyces verdensis*, Dietz and Li sp.n., NRRL 12256.

Antibiotic U-62,162 is active against various Gram-positive bacteria. Further, the base addition salts of antibiotic U-62,162 are also active against these bacteria. Thus, antibiotic U-62,162 and its salts can be used to disinfect washed and stacked food utensils contaminated with *S. aureus*. They can also be used as disinfectants on various dental and medical equipment contaminated with *S. aureus*. Still further, antibiotic U-62,162 and its salts can be used as a bacteriostatic rinse for laundered clothes, and for impregnating papers and fabrics; and they are also useful for suppressing the growth of sensitive organisms in plate assays and other microbiological media.

DETAILED DESCRIPTION OF THE INVENTION

Figure 2:
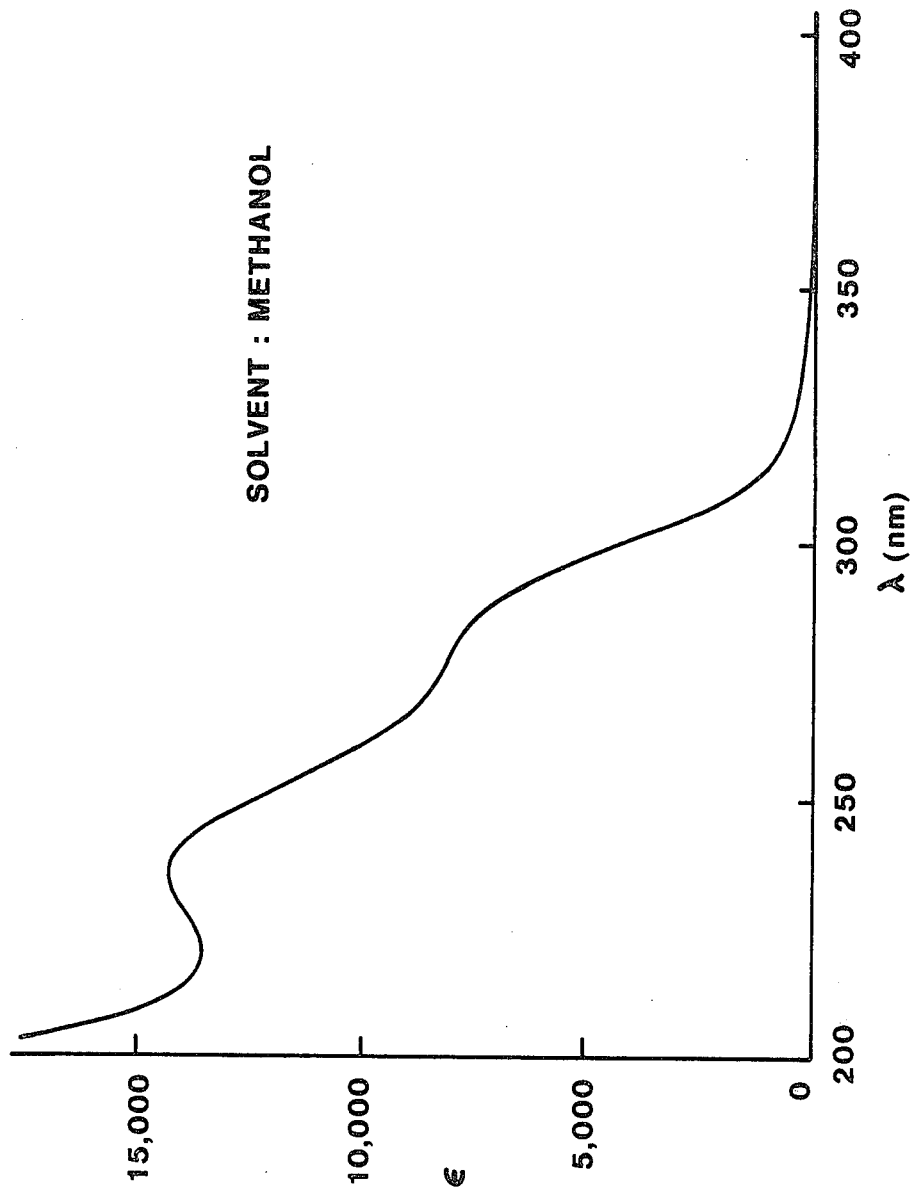

Chemical and Physical Properties of Antibiotic U-62,162:

Molecular Weight: 419 (high resolution spectrometry)
Molecular Formula: $C_{23}H_{33}NO_6$.
Color and Form of Crystals: Off-white needles.
Ultraviolet Absorption Spectrum:

The UV spectrum of antibiotic U-62,162 is shown in FIG. 2 of the drawings. The solution of antibiotic U-62,162 in methanol displayed absorption as follows:

| Solvent | λ max | a | Absorptivity(ε) |
|---|---|---|---|
| Methanol | 235 nm | 34.36 | 14,400 |
|  | 276 sh | 19.49 | 8,150 |
| 0.01N H$_2$SO$_4$ in MeOH | 232 | 35.17 | 14,750 |
|  | 276 | 19.37 | 8,100 |

Figure 1:
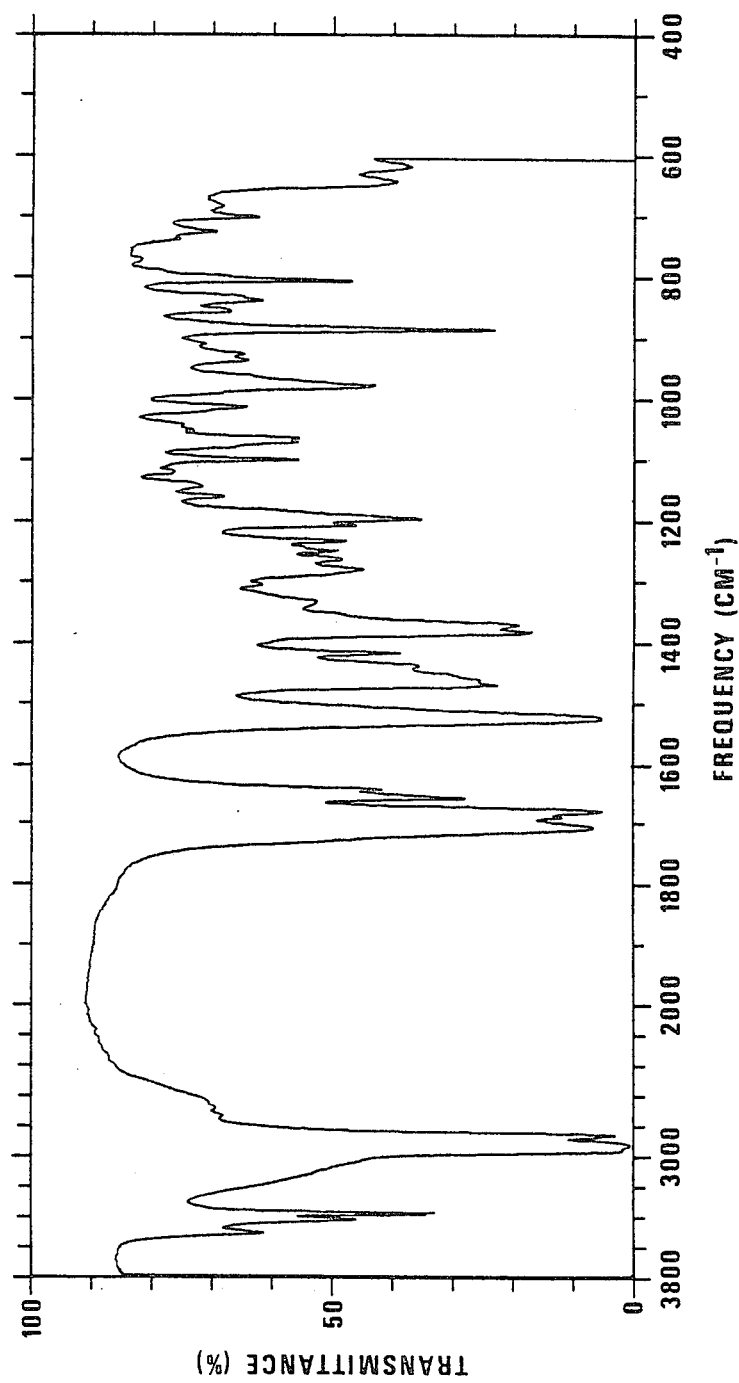

Melting Point: 96°–98°.
Infrared Absorption Spectrum:

Antibiotic U-62,162 has a characteristic infrared absorption spectrum in a mineral oil mull as shown in FIG. 1 of the drawings. Peaks are observed at the following wave lengths.

| Band Frequency[1] | Intensity[2] | Band Frequency | Intensity |
|---|---|---|---|
| 3511 | 61 | 1191 | 35 |
| 3420 | 46 | 1156 | 68 |
| 3388 | 34 | 1140 | 71 |
| 3374 | 32 | 1115 | 76 |
| 3025 | 45, sh. | 1096 | 55 |
| 2955 | 1 | 1066 | 55 |
| 2925 | 0 | 1060 | 55 |
| 2870 | 5 | 1046 | 73 |
| 2855 | 3 | 1038 | 74 |
| 2730 | 68 | 1009 | 64 |
| 2680 | 69 | 973 | 42 |
| 1702 | 6 | 933 | 64 |
| 1685 | 11 | 922 | 64 |
| 1675 | 5 | 906 | 71 |
| 1653 | 27 | 882 | 23 |
| 1638 | 41 | 853 | 66 |
| 1518 | 5 | 834 | 61 |
| 1465 | 22 | 801 | 47 |
| 1457 | 25 | 767 | 82 |
| 1434 | 35 | 733 | 75 |
| 1414 | 38 | 720 | 69 |
| 1378 | 16 | 697 | 62 |
| 1366 | 19 | 679 | 68 |
| 1328 | 52 | 638 | 39 |
| 1300 | 61 | 614 | 37 |
| 1276 | 44 |  |  |
| 1260 | 48 |  |  |
| 1246 | 48 |  |  |
| 1230 | 47 |  |  |
| 1203 | 45 |  |  |

[1]Wavenumbers (cm$^{-1}$)
[2]Percent transmittance (% T), sh, = shoulder.

Figure 4:
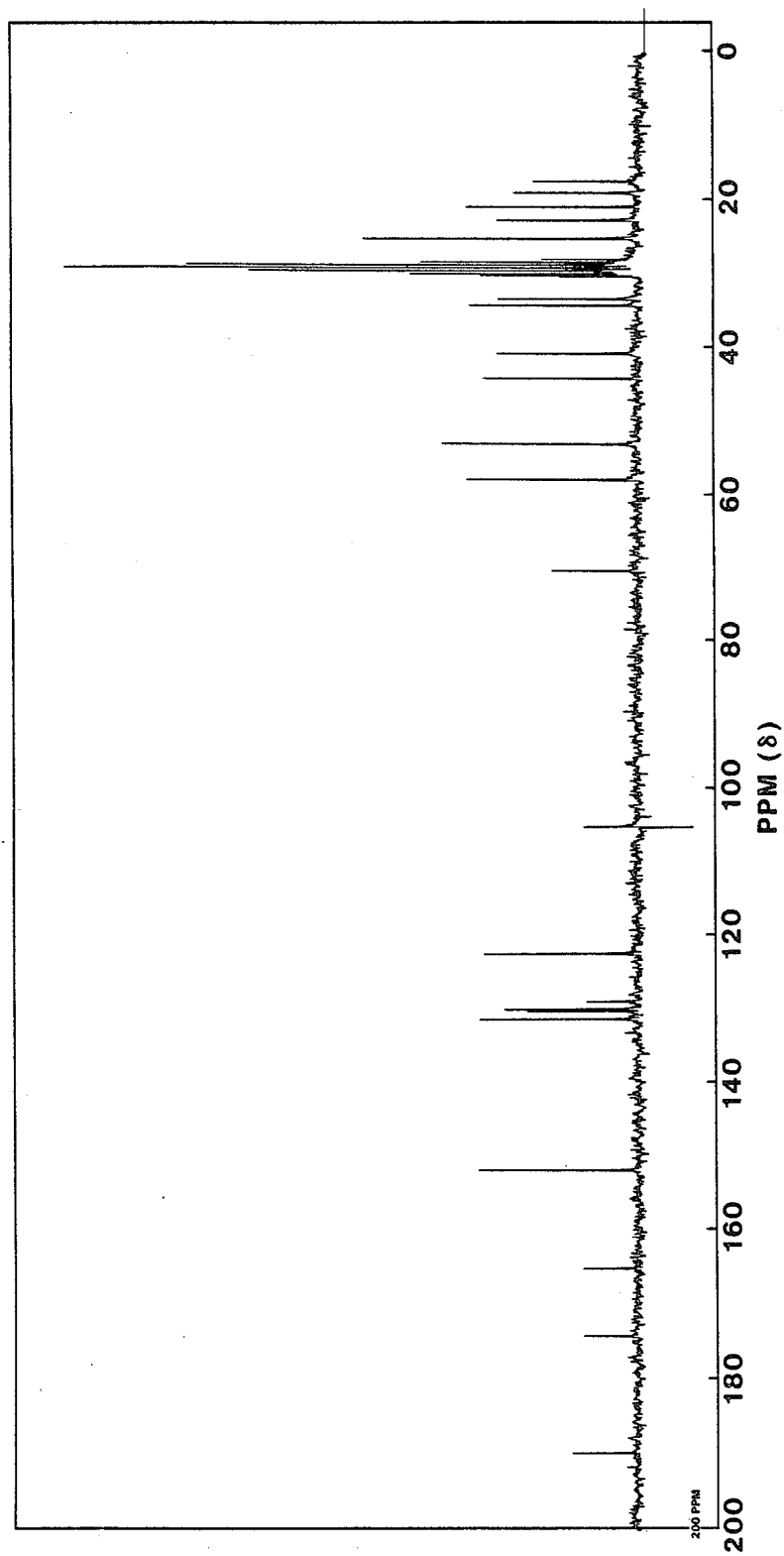

Intensity at 3800 cm$^{-1}$ is 85%T.
Minimum intensity at 1993 cm$^{-1}$ is 91% T.
$^{13}$C-Nuclear Magnetic Resonance (NMR) Spectrum:

The $^{13}$C-NMR spectrum of antibiotic U-62,162 is shown in FIG. 4 of the drawings. The $^{13}$C-NMR spectrum was observed on a Varian CFT-20 Spectrometer on a solution (ca. 0.5 ml., ca. 200 mg./ml.) of the sample of the antibiotic in deutero-acetone (d$_6$-acetone). The spectrum was calibrated against internal tetramethylsilane and frequencies were recorded in ppm downfield from tetramethylsilane.

Figure 3:
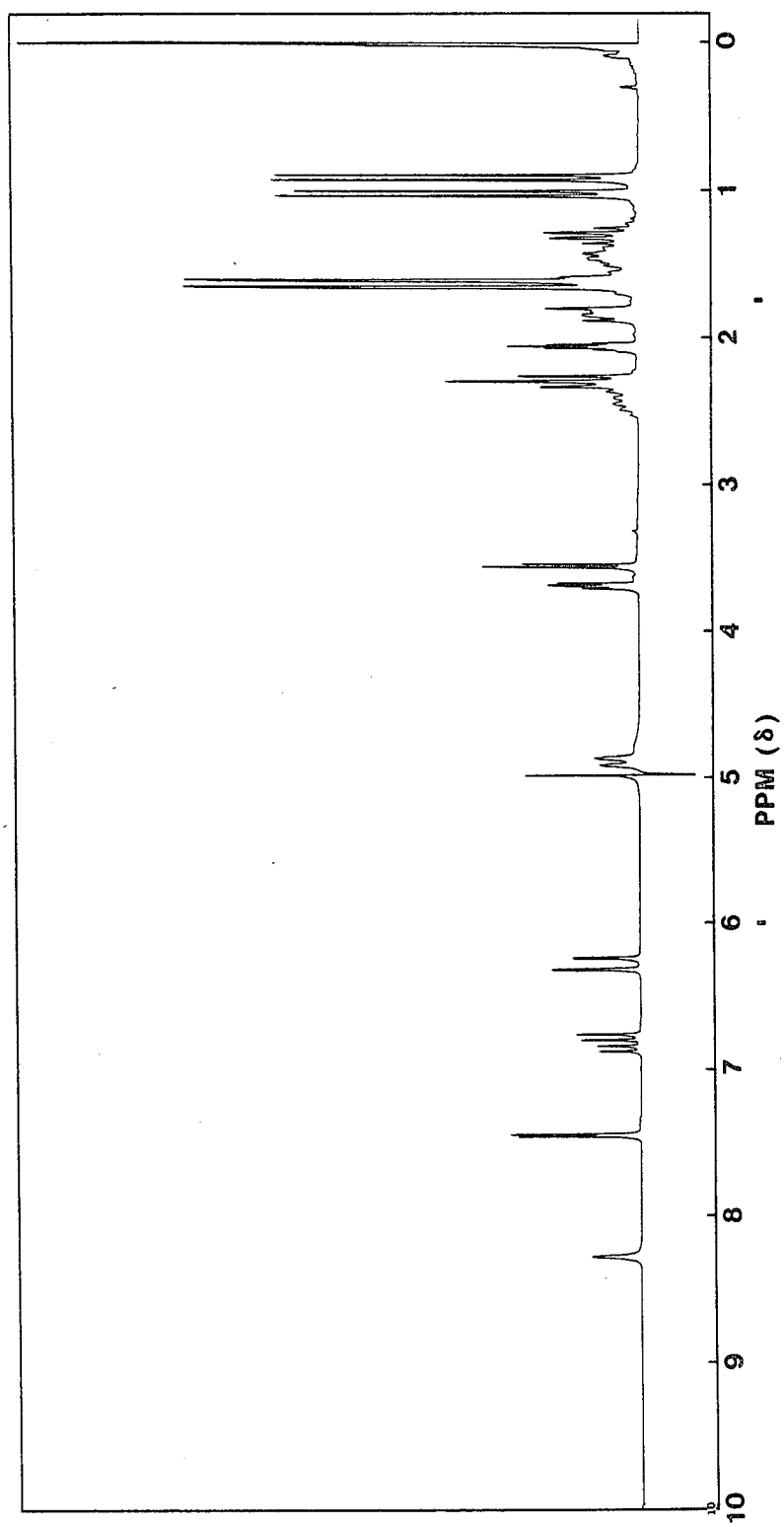

Proton Magnetic Resonance ($^1$H-NMR) Spectrum:

The $^1$H-NMR spectrum of antibiotic U-62,162 at 100 MHZ is shown in FIG. 3 of the drawings. The $^1$H-NMR spectrum was observed on a Varian XL-100-15 Spectrometer on a solution (ca. 0.5 ml., ca. 150 mg./ml.) of the sample of the antibiotic in deutero-acetone (d$_6$-acetone). The spectrum was calibrated against internal tetramethylsilane and frequencies were recorded in ppm downfield from tetramethylsilane.

Solubilities:

Antibiotic U-62,162 is soluble in lower alcohols (1–4 carbons), esters, for example, ethylacetate and methylacetate, ethers, for example, diethylether, tetrahydrofuran and dioxane, aromatic hydrocarbons, for example, benzene and toluene, dimethylformamide and dimethylsulfoxide, and lower ketones (3–6 carbons).

Antimicrobial Spectrum of Antibiotic U-62,162:

Antibiotic U-62,162 is active against various Gram-positive bacteria as shown in the following tables.

Assay:

The antibacterial assay is a standard agar dilution assay. The MIC is determined by standard methods using two-fold dilutions of the antibiotic in Brain Heart Infusion Broth (Difco Lab., Detroit, Michigan). The inocula are overnight cultures of the test organisms, diluted so that the final population contains approximately 10$^5$ cells/ml. The solutions are incubated at 28° to 37° C. for 24 hours. The lowest antibiotic concentration which allows no growth = MIC or minimum inhibitory concentration.

| Microorganism | | Minimum Inhibitory Concentration (mcg/ml) |
|---|---|---|
| *Staphylococcus aureus* | UC 76 | 1.0 |
| *Staphylococcus aureus* | UC 6685 | 1.0 |
| *Staphylococcus aureus* | UC 6690 | 1.0 |
| *Streptococcus pyogenes* | UC 152 | 125 |
| *Streptococcus faecalis* | UC 694 | 7.8 |
| *Enterococcus sp.* | UC 701 | 7.8 |
| *Escherichia coli* | UC 45 | >1000 |
| *Klebsiella pneumoniae* | UC 58 | >1000 |
| *Salmonella schottmuelleri* | UC 126 | >1000 |
| *Pseudomonas aeruginosa* | UC 95 | >1000 |

| Microorganism | | Minimum Inhibitory Concentration (mcg/ml) |
|---|---|---|
| *Streptococcus pneumoniae* | UC 41 | 1.0 |

Antibiotic U-62,162 was also tested for activity against a group of ampicillin-resistant and ampicillin-susceptible *H. influenzae* type b. The following results show that U-62,162 has moderate activity against all of the cultures tested.

A solution of the compound was prepared in dimethylsulfoxide (DMSO), diluted in Brain Heart Infusion Broth (BHIB) and MIC's were determined using the standard agar-dilution method.

| Organism | UC# | MIC (μg/ml) |
|---|---|---|
| H. influenzae | 6582* | 31.25 |
| H. influenzae | 6583* | 31.25 |
| H. influenzae | 6585* | 31.25 |
| H. influenzae | 6586* | 31.25 |
| H. influenzae | 6587* | 31.25 |
| H. influenzae | 6589* | 31.25 |
| H. influenzae | 6592* | 15.6 |
| H. influenzae | 6595* | 31.25 |
| H. influenzae | 6596* | 31.25 |
| H. influenzae | 6597+ | 31.25 |
| H. influenzae | 6598+ | 31.25 |
| H. influenzae | 6482+ | 62.5 |
| H. influenzae | 6483* | 31.25 |
| H. influenzae | 6484* | 31.25 |
| H. influenzae | 6485+ | 31.25 |
| H. influenzae | 6486+ | 31.25 |

*Ampicillin - resistant
+Ampicillin - susceptible

"UC" is a registered trademark of The Upjohn Company Culture Collection. These cultures can be obtained from The Upjohn Company, Kalamazoo, Mich., upon request.

THE MICROORGANISM

The microorganism used for the production of antibiotic U-62,162 is a biologically pure culture of *Streptomyces verdensis*, Dietz and Li sp.n., NRRL 12256.

A subculture of this microorganism can be obtained from the permanent collection of the Northern Regional Research Laboratory, U.S. Department of Agriculture, Peoria, Ill., U.S.A. Its accession number in this depository is NRRL 12256. It should be understood that the availability of the culture does not constitute a license to practice the subject invention in derogation of patent rights granted with the subject instrument by governmental action.

The microorganism of this invention was studied and characterized by Alma Dietz and Grace P. Li of The Upjohn Research Laboratories.

*Streptomyces verdensis*, Dietz and Li sp.n., which produces antibiotic U-62,162, is characterized and considered to be a new species of the genus Streptomyces. The culture conforms to the general characteristics of the genus (Pridham, T. G. and H. D. Tresner, 1974, Part 17, Actinomycetes and related organisms. Family VII. Streptomycetaceae Waksman and Henrici 1943. Genus I. Streptomyces. p. 748. In R. E. Buchanan and N. E. Gibbons (ed.), Bergey's Manual of Determinative Bacteriology, 8th ed., the Williams and Wilkins Co., Baltimore) but can be readily differentiated from described species of the genus (Pridham, T. G. and H. D. Tresner, 1974, Part 17, Actinomycetes and related organisms. Family VII. Streptomycetaceae Waksman and Henrici 1943. Genus I. Streptomyces. Table 17.46a–d Green Series. p. 825. In R. E. Buchanan and N. E. Gibbons (ed.), Bergey's Manual of Determinative Bacteriology, 8th ed. The Williams and Wilkins Co., Baltimore), in literature and patent descriptions available to us, and from cultures in the Upjohn Culture Collection (UC®). It can also be differentiated from cultures cited in Skerman et al. (Skerman, V. B. D., V. McGowan, and P. H. A. Sneath. 1980. Approved lists of bacterial names. Int. J. of Syst. Bacteriol. 30:225–420).

The culture belongs to the distinctive "green group cultures" cited in Argoudelis et al. (Argoudelis, A. D., J. H. Coats, and T. R. Pyke. 1972. Lincomycin production. U.S. Pat. No. 3,697,380) and in Hanka et al. (Hanka, L. J., A. Dietz, S. A. Gerpheide, S. L. Kuentzel, and D. G. Martin. 1978. CC-1065 (NSC-298233), A new antitumor antibiotic. Production, in vitro biological activity, microbiological assays and taxonomy of the producing microorganism. J. Antibiotics. 31:1211–1217). It is most similar to, but can be differentiated from, the subject cultures *S. espinosus* and *S. zelensis* of the last two references. This is shown in Table 4. On the basis of its color pattern it falls into a new color group orange yellow, gray, orange yellow in the Key for Identification of Actinomycetes with Emphasis on Streptomyces [Barnes, R. E., A. Dietz, and G. P. Li. 1980. Key for identification of actinomycetes with emphasis on the genus Streptomyces, p. 56–140. In A. Dietz and D. W. Thayer (ed.), Actinomycete Taxonomy (Procedures for Studying Aerobic Actinomycetes with Emphasis on the Streptomycetes). SIM Special Publication Number 6. Soc. for Ind. Microbiol. Arlington, VA.]. The new soil isolate has a distinctive green color on maltose-tryptone agar. Because of this distinctive color we propose that the culture, which is considered a new streptomycete species, be designated *Streptomyces verdensis* Dietz and Li sp.n. The name is derived from "verde" the Spanish name for "green."

Color Characteristics.

Aerial growth predominantly gray-green to gray. Melanin-negative. The primary reference colors of the culture on Ektachrome [Dietz. A. and D. W. Thayer (ed.). 1980. Actinomycete Taxonomy (Procedures for Studying Aerobic Actinomycetes with Emphasis on the Streptomycetes). SIM Special Publication Number 6. Soc. for Ind. Microbiol. Arlington, VA.] are given in Table 1. Secondary reference colors are given in Table 2. The culture may be placed in the yellow (Y) and green (GN) color series of Tresner and Backus (Tresner, H. D., and E. J. Backus. 1963. System of color wheels for streptomycete taxonomy. Appl. Microbiol. 11:335–338.

Microscopic Characteristics.

Spore chains short, straight to flexuous to open spiral. Spores are appressed and are predominantly spherical. The spore surface is spiny to hairy.

General Cultural Characteristics.

See Table 3.

Carbon Utilization.

Growth on carbon compounds was determined by the procedures of Shirling and Gottlieb (Shirling, E. B., and D. Gottlieb. 1966. Methods for characterization of *Streptomyces* species. Int. J. Syst. Bacteriol. 16:313–340). The culture grew well on the positive control, D-glucose. It also exhibited strong utilization of D-xylose, inositol, D-mannitol, D-fructose, and rhamnose.

Growth was positive on L-arabinose and doubtful on sucrose and raffinose. The culture did not grow on cellulose or the negative control, basal medium without added carbon compound.

Temperature.

Growth was good at 24°-37° C., moderate at 18° and 45° C. and doubtful at 55° C. Media used for temperature studies were Bennett's, Czapek's sucrose, and maltose-tryptone agars.

Whole Cell Analysis.

L-diaminopimelic acid was detected.

Antibiotic-Production.

The culture produces antibiotic U-62,162.

Culture Source.

Soil from Arkansas.

Type Strain.

*Streptomyces verdensis* NRRL 12256.

The methods used were those cited in Becker et al. (Becker, B., M. P. Lechevalier, and H. A. Lechevalier. 1966. Chemical composition of cell wall preparations from strains of various form-genera of aerobic actinomycetes. Appl. Microbiol. 13:236–243.), Dietz (Dietz, A. 1954. Ektachrome transparencies as aids in actinomycete classification. Ann. N. Y. Acad. Sci. 60:152–154; Dietz, A. 1967. *Streptomyces steffisburgensis* sp. n. J. Bacteriol. 94:2022–2026), Dietz and Mathews (Dietz, A., and J. Mathews. 1971. Classification of Streptomyces spore surfaces into five groups. Appl. Microbiol. 21:527–533), and in part those cited in Shirling and Gottlieb (Shirling, E. G., and D. Gottlieb. 1966. Methods for characterization of Streptomyces species. Int. J. Syst. Bacteriol. 16:313–340). All of the above have been incorporated in Dietz and Thayer [Dietz, A., and D. W. Thayer (ed.). 1980. Actinomycete Taxonomy (Procedures for Studying Aerobic Actinomycetes with Emphasis on the Streptomycetes). SIM Special Publication Number 6. Soc. for Ind. Microbiol. Arlington, VA].

TABLE 1

Primary Reference Color Characteristics[a] of *Streptomyces verdensis* (Appearance on Ektachrome[b])

| Agar Medium | Surface Chip No. | Surface Color Name | Reverse Chip No. | Reverse Color Name |
|---|---|---|---|---|
| Bennett's | 89 | pale yellow | 83 | brilliant yellow |
| Czapek's sucrose | 264 | light gray | 264 | light gray |
| Maltose-tryptone | 149 | pale green | 88 | dark yellow |
| Peptone-iron | 68 | strong orange yellow | 68 | strong orange yellow |
| 0.1% Tyrosine | 93 | yellowish gray | 73 | pale orange yellow |
| Casein Starch | 148 | very pale green | 90 | grayish yellow |

[a]Cultures were photographed on Ektachrome after seven days incubation at 28° C. Color determination was based on comparison with NBS color chips (SP 440. Color: Universal Language and Dictionary of Names. U.S. Government Printing Office, Washington, D.C. 20402; SPM 2106. ISCC-NBS Centroid Color Charts. Office of Standard Reference Material, Room B311, Chem. Building, National Bureau of Standards, Washington, D.C. 20234).
[b]Dietz, A. and D. W. Thayer (ed.) 1980. Actinomycete Taxonomy (Procedures for Studying Aerobic Actinomycetes with Emphasis on the Streptomycetes). SIM Special Publication Number 6. Soc. for Ind. Microbiol. Arlington, VA.

TABLE 2

| Secondary Reference Color[a] Agar Medium | Determination | Characteristics of *Streptomyces verdensis* Chip No. | Color Name |
|---|---|---|---|
| Bennett's | S | 112 | light olive gray |
|  | R | 70 | light orange yellow |
|  | P | — | — |
| Czapek's sucrose | S | 112 | light olive gray |
|  | R | 93 | yellowish gray |
|  | P | — | — |
| Maltose-tryptone | S | 122 | grayish yellow green |
|  | R | 70 | light orange yellow |
|  | P | — | — |
| Yeast extract-malt extract (ISP-2) | S | 109 | light grayish olive |
|  | R | 70 | light orange yellow |
|  | P | — | — |
| Oatmeal (ISP-3) | S | 109 | light grayish olive |
|  | R | 73 | pale orange yellow |
|  | P | — | — |
| Inorganic salts starch (ISP-4) | S | 122 | grayish yellow green |
|  | R | 73 | pale olive yellow |
|  | P | 79 | grayish yellow brown |
| Glycerol-asparagine (ISP-5) | S | 122 | grayish yellow green |
|  | R | 90 | grayish yellow |
|  | P | — | — |

S = Surface; R = Reverse; P = Pigment
[a]Color determinations made after fourteen days incubation at 28° C. Color determination based on comparison with NBS color chips (SP 440. Color: Universal Language and Dictionary of Names. U.S. Government Printing Office, Washington, D.C. 20402; SPM 2106. ISCC-NBS Centroid Color Charts. Office of Standard Reference Material, Room B311, Chem. Building, National Bureau of Standards, Washington, D.C. 20234).

TABLE 3

General Cultural Characteristics of Streptomyces verdensis

| Medium | Surface Color | Reverse Color | Pigment | Other Characteristics |
|---|---|---|---|---|
| Agar Peptone-Iron | Heavy gray-green | Olive tan | — | Melanin negative |
| Calcium malate | Pale gray | Cream | — | Malate solubilized |
| Glucose asparagine | Gray-green with feathery colorless edge | Light green | — | — |
| Skim milk | Grayish vegetative | Orange | Orange | Casein solubilized |
| Tyrosine | Gray-green | Olive yellow-tan | Light tan | Tyrosine solubilized |
| Xanthine | Gray-green | Olive yellow | Light tan | Xanthine not solubilized |
| Nutrient starch | Gray-green | Greenish yellow | — | Starch solubilized |

TABLE 3-continued

General Cultural Characteristics of Streptomyces verdensis

| Medium | Surface Color | Reverse Color | Pigment | Other Characteristics |
|---|---|---|---|---|
| Yeast extract-malt extract | Heavy gray-green | Olive-yellow-tan | Light olive-yellow-tan | — |
| Peptone-yeast extract-iron (ISP-6) | Trace pink-white on colorless vegetative | Tan | — | Melanin negative |
| Tyrosine (ISP-7) | Gray-green to gray | Gray-green-cream | — | Melanin negative |
| Gelatin | | | | |
| Plain | Pink-cream surface ring | — | Trace olive | Liquifaction-¾ |
| Nutrient | Pink-cream surface ring | — | Pale yellow-tan | Liquifaction-¾ |
| Broth | | | | |
| Synthetic nitrate | — | — | — | Colorless flocculent bottom growth. Nitrate reduced to nitrite. |
| Nutrient nitrate | Colorless pellicle | — | — | Pale yellow flocculent bottom growth. Nitrate reduced to nitrite. |
| Litmus milk | Blue surface ring with trace white aerial | — | Purple | Trace peptonization pH 7.39 |

TABLE 4

Differentiation of S. verdensis, S. zelensis and S. espinosus

| Growth Condition | S. verdensis | S. zelensis | S. espinosus |
|---|---|---|---|
| Calcium malate agar | Malate solubilized | Malate not solubilized | Malate not solubilized |
| Synthetic nitrate broth | Reduction | Reduction | No reduction |
| Gelatin Liquefaction | Partial | Complete | Partial |
| Growth on Carbon Compounds in Synthetic Medium: | | | |
| L-arabinose | Moderate | Moderate | Heavy |
| Surcose | Doubtful | None | None |
| Rhamnose | Heavy | None | Heavy |
| Raffinose | Doubtful | None | None |
| Temperature Range | 18–45C | 18C–45C | 18C–55C |
| Antibiotics Produced | U-62,162 | CC-1065 | Lincomycin |
| Spore Surface | Spiny to hairy | Spiny or thorny | Thorny to spiny to hairy |
| Spores | Appressed and also disseminated | Appressed | Well differentiated |
| Bottom tube colors. Key based on color pattern | Orange yellow, gray, orange yellow (New color group) | Yellowish brown, greenish yellow, yellow | Orange yellow, grey, reddish orange |

[a]Barnes, R. E., A. Dietz, and G. P. Li. 1980. Key for identification of actinomycetes with emphasis on the genus Streptomyces, p. 56-140. In A. Dietz and D. W. Thayer (ed.). Actinomycete Taxonomy (Procedures for Studing Aerobic Actinomycetes with Emphasis on the Streptomycetes). SIM Special Publication Number 6. Soc. for Ind. Microbiol. Arlington, Va.

The compound of the invention process is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compound by the invention process can be effected at any temperature conducive to satisfactory growth of the microorganism, for example, between about 18° and 40° C., and preferably between about 20° and 28° C. Ordinarily, optimum production of the compound is obtained in about 1 to 5 days. It is critical that the fermentation pH be controlled below 8.5 because U-62,162 is unstable at this pH and higher.

When growth is carried out in large vessels and tanks, it is preferable to use the vegetative form, rather than the spore form, of the microorganism for inoculation to avoid a pronounced lag in the production of the compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compound, so long as a good growth of the microorganism is obtained.

A variety of procedures can be employed in the isolation and purification of the compound produced by the subject invention from fermentation beers. Isolation can be accomplished by extraction with solvents such as methylene chloride, butanol, ethyl acetate and the like; and silica gel chromatography can be used to purify crude preparations of the antibiotic.

In a preferred recovery process, the compound produced by the subject process is recovered from the culture medium by separation of the mycelia and undissolved solids by conventional means, such as by filtration or centrifugation and solvent extraction of the filtered broth. The filtrate can be extracted with a solvent for antibiotic U-62,162, for example, methylene chloride, and the extract evaporated under reduced pressure to an aqueous concentrate. This preparation can be purified by chromatography on silica gel. The solvent system used for the chromatography is $CHCl_3$:MeOH (94:6) (v/v). The solvent system toluene::absolute ethanol (97:3) can also be used.

Further purification is achieved by use of countercurrent distribution using an appropriate solvent system, for example, ethylacetate:ethanol (95%):cyclohexane:-water (2:3:3:2, v/v). Material obtained from this purification can be recrystallized from a suitable solvent, for example, ethylacetate and Skellysolve B mixtures to afford essentially pure antibiotic U-62,162.

Salts of antibiotic U-62,162 can be formed with inorganic or organic bases. Such salts can be prepared, as for example, by suspending antibiotic U-62,162 in water, adding one mole equivalent of a base, and freeze-drying to provide a dried residue consisting of the U-62,162 salt. Antibiotic U-62,162 salts with inorganic cations which can be formed include the sodium, potassium, and calcium salts. Other salts of U-62,162, including those with inorganic bases such as primary, secondary, and tertiary monoamines as well as with polyamines, also can be formed using the above-described or other commonly employed procedures. Other valuable salts are obtained with therapeutically effective bases which impart additional therapeutic effects thereto. Such bases are, for example, the purine bases such as theophyllin, theobromine, caffeine, or derivatives of such purine bases; antihistaminic bases which are capable of forming salts with weak acids, pyridine compounds such as nicotinic acid amide, isonicotinic acid hydrazide and the like; phenylalkylamines such as Adrenaline, ephedrine, and the like; choline, and others. Salts of U-62,162 can be used for the same biological purposes as the parent compound.

The following examples are illustrative of the process and product of the invention, but are not to be construed as limiting. All percentages are by weight and all solvent mixture proportions are by volume unless otherwise noted.

EXAMPLE 1

A. Fermentation

A biologically pure culture of *Streptomyces verdensis* Dietz and Li sp.n., NRRL 12256, is used to inoculate 500-ml. Erlenmeyer flasks containing 100 ml of sterile medium of the following composition:

|  | g/liter |
|---|---|
| Glucose monohydrate | 25.0 |
| Pharmamedis | 25.0 |
| Tap water, q.s. | 1 liter |

The seed medium post-sterilization pH is ~6.5. The seed inoculum is grown for three days at 28° C. on a Gump rotary shaker operating at 250 rpm and having a 2½ inch stroke.

Seed inoculum, prepared as above, is used to inoculate the fermentation at 5% rate. The fermentation is conducted in a Virtis fermenter equipped with a continuous pH control and set to maintain the pH of the fermentation between 6.5 and 7.5. The aeration rate is 6 liters of air/min., using a 15 liter fermenter vessel with 10 liters of the fermentation medium and maintaining the temperature at 28° C. Fermentation medium has the following composition:

|  | g/liter |
|---|---|
| Brer Rabbit Molasses | 30.0 |
| Cerelose | 5.0 |
| Wilson's Liquid Pepton | 10.0 |
| Sodium glutamate | 2.0 |
| Calcium carbonate | 5.0 |
| Tap water, pH adjusted to 7.0 prior to sterilization. | |

B. Recovery

A 4-liter quantity of whole beer prepared as described above, is filtered at beer pH (pH 7.25) without addition of filteraid, affording 3850 ml of filtered beer, 4 BU/ml (*S. aureus* 6029). The filtrate is then acidified to pH 4.5 using 6 N $H_2SO_4$ with efficient agitation. It is extracted twice, first with 1500 ml of methylene chloride, then with 1000 ml of that solvent. The combined extracts are washed with 500 ml of water and evaporated to dryness on a rotary evaporator at a pot temperature of 30°. The residue, 270 mg, assayed 37 BU/mg of antibiotic U-62,162.

C. Purification (1) Chromatography

Buffered (pH 5.8) silica gel is prepared by treating 1 kg of silica gel 60 with a solution of 54.4 g of $KH_2PO_4$ in 800 ml of water. This is dried 16 hours at 110°. A 1 inch (diameter) column containing 60 g of buffered (pH 5.8) silica gel is poured in a slurry with chloroform. To this is added 250 mg of crude U-62,162, prepared as described above, in chloroform. The column is developed first with 120 ml of $CHCl_3$, then with $CHCl_3$:MeOH (94:6 v/v). Fractions of 5 ml each are collected beginning when the mixed solvent is introduced. They are assayed by plating 12 mm discs containing 80 ml aliquots on S. aureus 6029 trays. Fractions 55–65, containing most of the activity, are pooled and evaporated, 90 mg, 182 BU/mg, 17,200 total BU.

(2) Countercurrent Distribution:

A preparation of antibiotic U-62,162, as described above, (3 g) is distributed for 300 transfers in the two-phase solvent system afforded by ethyl acetate:ethanol (95%):cyclohexane:water (2:3:3:2 v/v). Phase volumes are 10 ml each. Fractions 120–150 are combined and the residue from these after evaporation affords essentially pure crystalline antibiotic U-62,162, 1 g, assaying 800–1500 BU/mg against *S. aureus* 6029. A BU is the amount of material distributed on a 12 mm disc which will give a 20 mm zone of inhibition.

(3) Recrystallization

Crystalline antibiotic U-62,162, obtained as described above, is recrystallized by dissolving 100 mg in 1 ml of ethylacetate and diluting with Skellysolve B (isomeric hexanes) until cloudiness results from crystal formation. The crystals are recovered by standard methods.

I claim:

1. Antibiotic U-62,162, which is active against Gram-positive bacteria, and which in its essentially pure crystalline form has the following characteristics:
   (a) molecular weight of 419.2303 (high resolution mass spectrometry);
   (b) is soluble in lower alcohols (1–4 carbons), esters, for example, ethylacetate and methylacetate, ethers, for example, diethylether, tetrahydrofuran and dioxane, aromatic hydrocarbons, for example, benzene and toluene, dimethylformamide and dimethylsulfoxide, and lower ketones (3–6 carbons);
   (c) a characteristic infrared absorption spectrum when dissolved in a mineral oil mull as shown in FIG. 1 of the drawings;
   (d) a characteristic UV spectrum as shown in FIG. 2 of the drawings;
   (e) a characteristic $^1$H-NMR spectrum as shown in FIG. 3 of the drawings;
   (f) a characteristic $^{13}$C-NMR spectrum as shown in FIG. 4 of the drawings;
   (g) a melting point of 96°–98°;
   (h) a molecular formula $C_{23}H_{33}NO_6$;
   (i) an elemental composition as follows: $C_{65.83}H_{7.93}N_{3.34}$; and base addition salts thereof.

2. A process for preparing antibiotic U-62,162 which comprises cultivating *Streptomyces verdensis* Dietz and Li sp. n., having the identifying characteristics of NRRL 12256, in an aqueous nutrient medium under aerobic conditions until substantial antibiotic U-62,162 activity is imparted to said medium.

3. A process, according to claim 2, wherein said aqueous nutrient medium contains a source of assimilable carbohydrate and assimilable nitrogen.

4. A process for recovering antibiotic U-62,162 from a fermentation beer *Streptomyces verdensis* Dietz and Li having the identifying characteristics of NRRL 12256, which comprises:
   (a) filtering said beer to obtain filtered beer containing antibiotic U-62,162;
   (b) adjusting the pH of the filtrate to about 4.5;
   (c) extracting said filtrate with a solvent for U-62,162 to obtain an extract containing antibiotic U-62,162;
   (d) evaporating said extract to an aqueous concentrate; and
   (e) purifying said extract first by chromatographic means and then by countercurrent distribution to obtain essentially pure antibiotic U-62,162.

5. A process, according to claim 4, wherein said filtered beer is extracted with methylene chloride.

6. A process, according to claim 4, wherein said aqueous concentrate is subjected to chromatography on silica gel using the solvent system $CHCl_3$, then $CHCl_3$:MeOH (94:6 v/v) to obtain essentially pure preparations of antibiotic U-62,162.

7. A process, according to claim 4, wherein the solvent system in the countercurrent distribution is ethylacetate:ethanol (95%):cyclohexane:water (2:3:3:2 v/v).

8. A biologically pure culture of the microorganism *Streptomyces verdensis* Dietz and Li sp.n., having the identifying characteristics of NRRL 12256, said culture being capable of producing the antibiotic U-62,162 in a recoverable quantity upon fermentation in an aqueous nutrient medium containing assimilable sources of carbon, nitrogen and inorganic substances.

* * * * *